(12) United States Patent
Parthasaradhi Reddy et al.

(10) Patent No.: US 10,464,931 B2
(45) Date of Patent: Nov. 5, 2019

(54) PROCESS FOR THE PREPARATION OF QUINOLIN-2(1H)-ONE DERIVATIVES

(71) Applicant: Honour (R&D), Erragadda, Hyderabad (IN)

(72) Inventors: Bandi Parthasaradhi Reddy, Hyderabad (IN); Kura Rathnakar Reddy, Hyderabad (IN); Bandi Vamsi Krishna, Hyderabad (IN); Kesireddy Subhash Chander Reddy, Hyderabad (IN); Guda Yadava Reddy, Hyderabad (IN)

(73) Assignee: Honour (R&D) (IN)

( * ) Notice: Subject to any disclaimer, the term of this patent is extended or adjusted under 35 U.S.C. 154(b) by 0 days.

(21) Appl. No.: 16/066,402

(22) PCT Filed: Dec. 28, 2016

(86) PCT No.: PCT/IB2016/058033
§ 371 (c)(1),
(2) Date: Jun. 27, 2018

(87) PCT Pub. No.: WO2017/115287
PCT Pub. Date: Jul. 6, 2017

(65) Prior Publication Data
US 2019/0010145 A1    Jan. 10, 2019

(30) Foreign Application Priority Data

Dec. 28, 2015 (IN) .......................... 6994/CHE/2015
Feb. 26, 2016 (IN) ............................ 201641006673

(51) Int. Cl.
*C07D 409/14* (2006.01)
*C07D 409/12* (2006.01)
*A61P 25/18* (2006.01)

(52) U.S. Cl.
CPC ........ *C07D 409/14* (2013.01); *C07D 409/12* (2013.01); *A61P 25/18* (2018.01)

(58) Field of Classification Search
CPC .................................................. C07D 409/14
USPC ........................................................ 549/19
See application file for complete search history.

(56) References Cited

U.S. PATENT DOCUMENTS 8,349,840 B2 *   1/2013   Yamashita ........... C07D 409/12
                                                  514/253.05

FOREIGN PATENT DOCUMENTS

| CN | 104829603 | * 12/2015 | ........... C07D 409/12 |
| CN | 104829603 A | 12/2015 | |
| WO | 2006112464 A1 | 10/2006 | |
| WO | WO 2017/106641 | * 12/2015 | ........... C07D 409/12 |

OTHER PUBLICATIONS

International Search Report for PCT/IB2016/058033 dated Nov. 4, 2017.

\* cited by examiner

*Primary Examiner* — Nizal S Chandrakumar
(74) *Attorney, Agent, or Firm* — Caesar Rivise, PC

(57) ABSTRACT

The present invention relates to quinolin-2(1H)-one derivatives polymorph and its process thereof. Formula (I).

9 Claims, 2 Drawing Sheets

PROCESS FOR THE PREPARATION OF QUINOLIN-2(1H)-ONE DERIVATIVES

FIELD OF THE INVENTION

The present invention relates to a process for the preparation of Quinolin-2(1H)-one derivative and its polymorphic form thereof.

BACKGROUND OF THE INVENTION

The Quinolin-2(1H)-one derivative is a heterocyclic compound having a specific substituent or substituents is known as an active ingredient that has serotonin uptake inhibitory activity (or serotonin re-uptake inhibitory activity) in addition to dopamine $D_2$ receptor partial agonistic activity ($D_2$ receptor partial agonistic activity), serotonin 5-$HT_{2A}$ receptor antagonistic activity (5-$HT_{2A}$ receptor antagonistic activity), and adrenaline $\alpha_1$ receptor antagonistic activity ($\alpha_1$ receptor antagonistic activity). This active ingredient has a wide therapeutic spectrum for central nervous system diseases (particularly schizophrenia). In the pharmaceutical field, the development of pharmaceutical preparations that are suitable according to the severity of disease in various patients in need of treatment, patient predisposition, and other factors, has been desired.

Brexpiprazole, which is a Quinolin-2(1H)-one derivative, having the chemical name 7-{4-[4-(1-Benzothiophen-4-yl) piperazin-1-yl]butoxy}quinolin-2(1H)-one a compound of formula I has been approved under the trade name Rexulti® as an Tablet, oral having the following dosage forms 0.25 MG, 0.5 MG, 1 MG, 2 MG, 3 MG, 4 MG.

Formula I

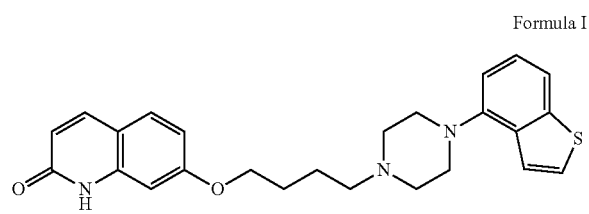 [SMILES: O=c1ccc2ccc(OCCCCN3CCN(c4cccc5sccc45)CC3)cc2[nH]1]

U.S. Pat. No. 7,888,362 B2 (U.S. Pat. No. '362) discloses Brexpiprazole and its pharmaceutically acceptable salts. U.S. Pat. No. '362 discloses the following scheme for the preparation of Brexpiprazole.

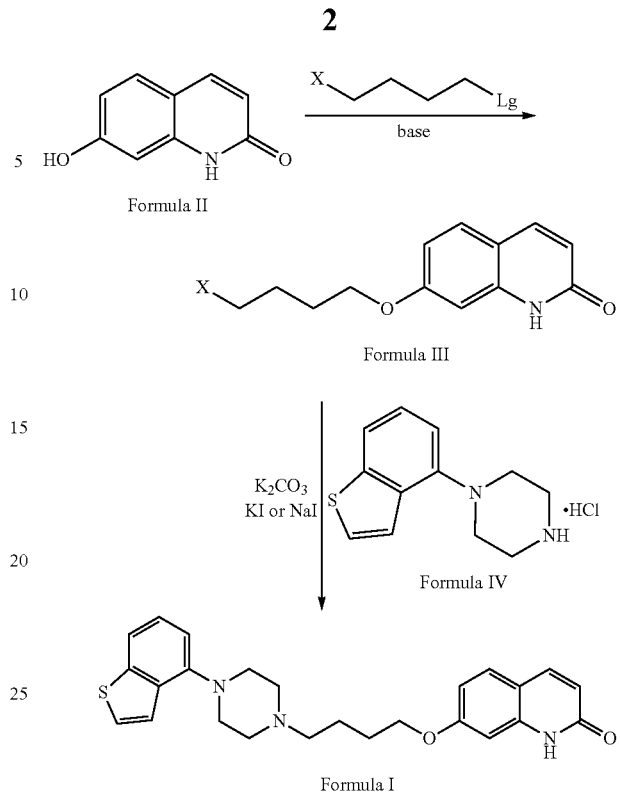

wherein X, Lg represents a halogen atom or a group, which causes a substitution reaction the same as in halogen atom.

The key intermediates in the preparation of Brexpiprazole are 7-Hydroxyquinoline-2(1H)-one a compound of formula II and 1-(benzo[b]thiophen-4-yl)piperazine hydrochloride of formula IV. One of the intermediate in the preparation of Brexpiprazole, 7-Hydroxyquinoline-2(1H)-one a compound of formula II was synthesized from Journal of Medicinal Chemistry Volume 58 Issue 14 Pages 5561-5578, WO 2014085284 A1, WO 2012003418 A2, WO 2002002108 A1 wherein discloses the preparation of Formula II by the reaction of N-(3-methoxyphenyl)cinnamamide with aluminum chloride at reflux temperature.

The provided prior art processes involves higher temperatures for the cyclization reaction as well as involves class 2 solvents, such as chlorobenzene, which have limitations in the use of these solvents as per the FDA ICH guidelines.

CN 104844585 A discloses the following scheme for the preparation of Brexpiprazole:

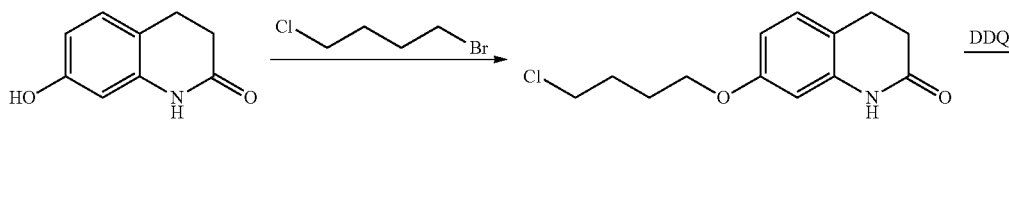

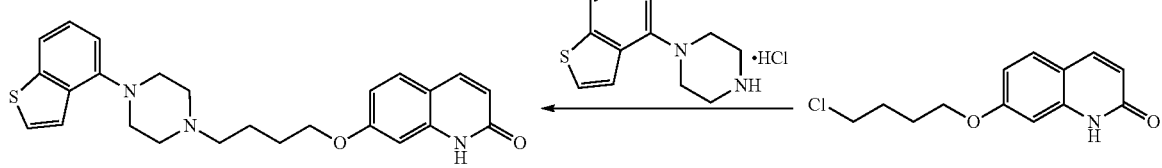

CN 104447723 A discloses the following scheme for the preparation of Brexpiprazole:

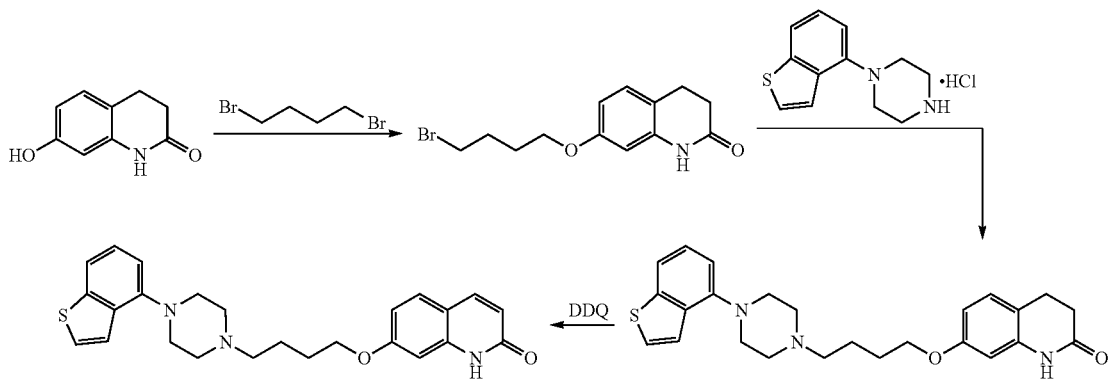

The present inventors have followed the above provided process and observed that if DDQ used in the final stages of the reaction impurities are formed, which are difficult to be removed and in turn results in low yield and low purity of the obtained product.

Another key intermediate involved in the preparation of Brexpiprazole is 1-(benzo[b]thiophen-4-yl)piperazine hydrochloride and was synthesized as follows:

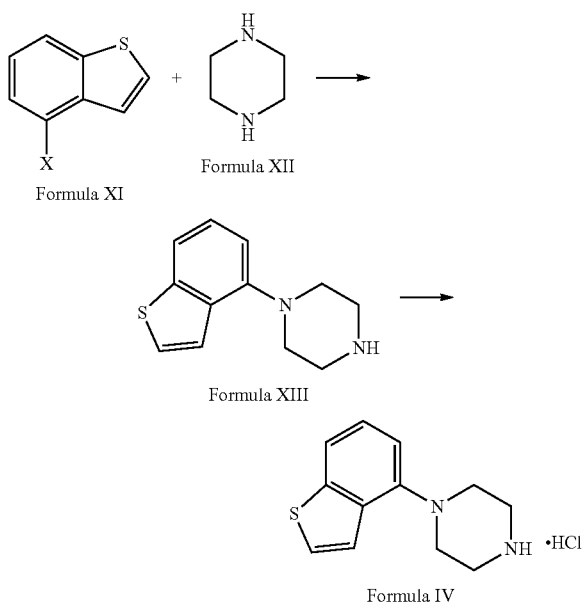

wherein X is a leaving group.

However the above reaction involves in the formation of dimer of formula X as impurity during the condensation of compound of formula XI and XII.

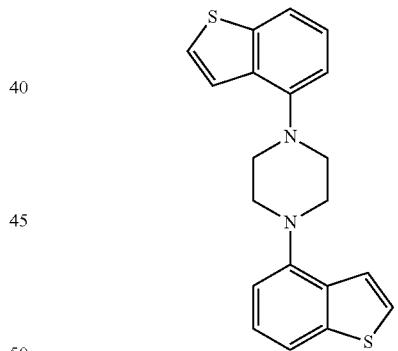

Formula X

U.S. Pat. No. '362, WO 2007026959 A2, WO 2008047883 A1, JP 4540700 B2, JP 4785881 B1, Organic Process Research & Development, Volume: 19, Issue: 4, Pages: 555-558, CN 104529998 A, WO 2015054976 A1, CN 104829602 A, CN104892589 A discloses the reaction of 1-(benzo[b]thiophen-4-yl)piperazine with conc. hydrochloric acid, wherein the purity of the obtained 1-(benzo[b]thiophen-4-yl)piperazine hydrochloride salt is low with significant amount of dimer impurity, which inevitably decreases the yield of final compound i.e., Brexpiprazole.

Further the prior art processes discloses the column purification methods to increase the purity of Brexpiprazole, however it is not commercially and industrially feasible.

U.S. Pat. No. 9,206,169 B2 (U.S. Pat. No. '169) discloses the preparation of 1-(benzo[b]thiophen-4-yl)piperazine by reacting compound of formula XI and XII in the presence of (a) a palladium compound and a tertiary phosphine or (b) a palladium carbene complex, in an inert solvent or without a solvent in order to suppress the by-product impurity. However, the process is not economical and cost-effective as the used palladium complexes are not easily available. Further after the reaction, the removal of by-products is not easy.

US 20150087655 A1 discloses Brexpiprazole dihydrate, anhydride and its process for the preparation thereof.

CN 104844586 A discloses Brexpiprazole amorphous form and its process for the preparation thereof.

CN 104829603 A discloses Brexpiprazole hydrochloride monohydrate and process for the preparation, wherein designated as Form A.

Polymorphism is defined as "the ability of a substance to exist as two or more crystalline phases that have different arrangement and/or conformations of the molecules in the crystal Lattice. Thus, in the strict sense, polymorphs are different crystalline structures of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning calorimetry (DSC) and Infrared spectrometry (IR).

Brexpiprazole and its hydrochloride salt can exist in different polymorphic forms which may differ from each other in terms of stability, physical properties, spectral data and methods of preparation. However, there is still a need for novel crystalline forms, which are more stable, reproducible and free of other polymorphic forms.

In view of the above the present inventors have now found a polymorph of Brexpirpazole hydrochloride, which is stable, having high purity and can be used as an intermediate in the preparation of Brexpiprazole.

Further the present inventors have observed that by incorporating these prior art processes the obtained yields of intermediates are low with the formation of by-products which thereby led to the low yields and low purity of Brexpiprazole.

Further there is a need for the improved, cost-effective, industrially applicable process for the preparation of Brexpiprazole having high yields and purity.

The present inventors have now found a process for preparation of Brexpiprazole, which resolves above referred issues and industrially suitable.

OBJECTIVES OF THE INVENTION

The objective of the present invention is to provide crystalline polymorph of Brexpiprazole hydrochloride and process for its preparation thereof.

Another objective of the present invention is to provide a process for the preparation of Brexpiprazole, which is industrially applicable and economically feasible.

Another objective of the invention is to provide process for the preparation of Brexpiprazole having high yields and purity.

SUMMARY OF THE INVENTION

The present invention relates to crystalline form of Brexpiprazole Hydrochloride designated as Form H, characterized by Powder X-Ray Diffraction, having peaks at about 12.5, 15.3, 18.2, 20.2°2θ±0.2 degrees.

The present invention also relates to a process for the preparation of Brexpiprazole Hydrochloride crystalline Form H, which comprises:

a. treating Brexpiprazole base in a solvent;

b. adjusting the pH with anhydrous hydrogen chloride; and c. isolating Brexpiprazole hydrochloride crystalline Form H.

The present invention also relates to process for the preparation of Brexpiprazole Hydrochloride, which comprises:

a. reacting compound of formula V,

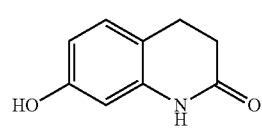

Formula V with 2,3-dichloro-5,6-dicyano-1,4-benzoquinone to obtain a compound of formula II;

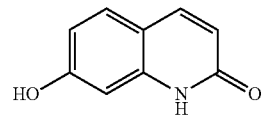

Formula II b. condensing the compound of formula II with compound of formula VI,

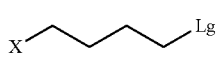

Formula VI wherein X, Lg represents a halogen atom or a group which causes a substitution reaction the same as in halogen atom to yield a compound of formula III;

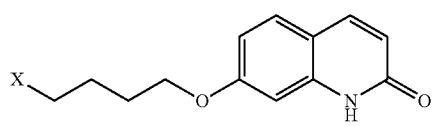

Formula III c. reacting the compound of formula XI

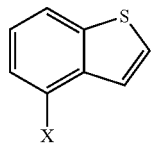

Formula XI wherein X is a leaving group
with piperazine compound of formula XII,

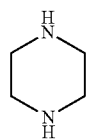

Formula XII to obtain a compound of formula XIII;

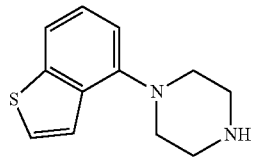

Formula XIII d. treating the compound of formula XIII with anhydrous hydrogen chloride to yield a compound of formula IV;

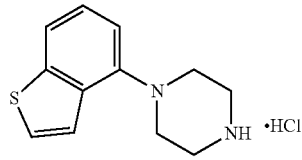

Formula IV e. optionally desalifying compound of formula IV;
f. condensing the compound of formula IV obtained as in step (d) or step (e) with formula III,

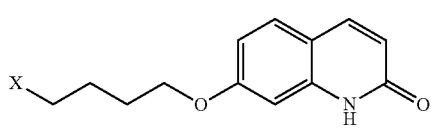

Formula III wherein X is a leaving group
to yield Brexpiprazole compound of formula I;
g. treating the obtained Brexpiprazole compound of formula I with anhydrous hydrogenchloride; and
h. converting to Brexpiprazole hydrochloride.

The present invention also relates to a process for the preparation of Brexpiprazole compound of Formula I, which comprises:

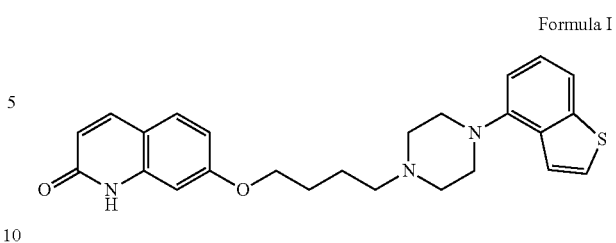

Formula I treating Brexpiprazole hydrochloride Form H with a base.

The present invention also relates to a process for the preparation of Brexpiprazole compound of Formula I, which comprises:

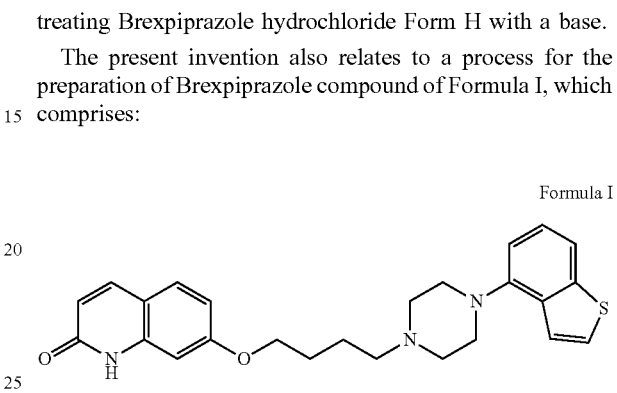

Formula I a. reacting compound of formula V with 2,3-dichloro-5,6-dicyano-1,4-benzoquinone in the presence of an organic solvent selected from polar aprotic solvent, at a temperature of 30-60° C. and having molar ratio of 2,3-dichloro-5,6-dicyano-1,4-benzoquinone to compound of formula V in the range of 0.5-2:1 to obtain a compound of formula II;

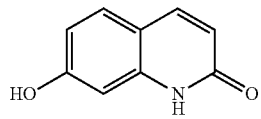

Formula II b. condensing the compound of formula II with compound of formula VI,

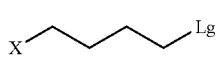

Formula VI wherein X, Lg represents a halogen atom or a group which causes a substitution reaction the same as in halogen atom
to yield a compound of formula III;

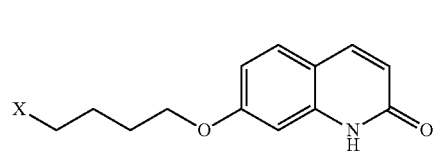

Formula III c. condensing the compound of formula III with compound of formula IV or free base;

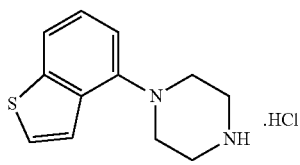
Formula IV to yield the compound of formula I;
d. converting Brexpiprazole compound of formula I to Brexpiprazole hydrochloride;
e. isolating Brexpiprazole hydrochloride Form H; and
f. converting Brexpiprazole hydrochloride Form H to Brexpiprazole.
wherein steps d to f are optional.

The present invention also relates to a process for the preparation of 7-Hydroxyquinoline-2(1H)-one of formula II, which comprises:

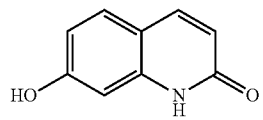
Formula II reacting the compound of formula V,

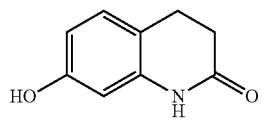
Formula V with 2,3-dichloro-5,6-dicyano-1,4-benzoquinone in the presence of an organic solvent, at a temperature of 30-60° C. and having molar ratio of 2,3-dichloro-5,6-dicyano-1,4-benzoquinone to compound of formula V in the range of 0.5-2:1.

The present invention also relates to a process for the preparation of Brexpiprazole compound of Formula I, which comprises:

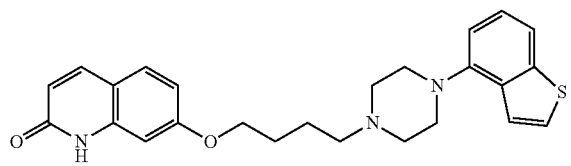
Formula I a. reacting the compound of formula XI,

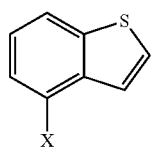
Formula XI wherein X is a leaving group with piperazine compound of formula XII,

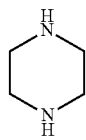
Formula XII to obtain a compound of formula XIII;

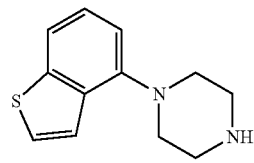
Formula XIII b. treating the compound of formula XIII with anhydrous hydrogen chloride to yield a compound of formula IV;

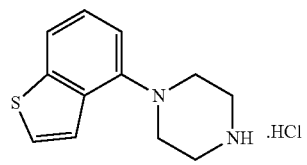
Formula IV c. optionally desalifying compound of formula IV;
d. condensing the compound of formula IV obtained as in step (b) or step (c) with formula III,

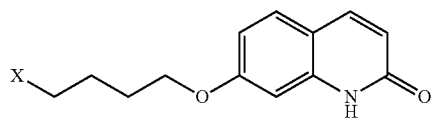
Formula III wherein X is a leaving group
to yield a compound of formula I;
e. converting Brexpiprazole compound of formula I to Brexpiprazole hydrochloride;
f. isolating Brexpiprazole hydrochloride Form H; and
g. converting Brexpiprazole hydrochloride Form H to Brexpiprazole.
wherein steps e to g are optional.

The present invention relates to a process for the preparation of 1-(benzo[b]thiophen-4-yl)piperazine hydrochloride salt of formula IV, which comprises:

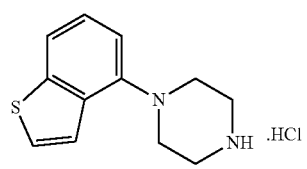
Formula IV a. reacting the compound of formula XI,

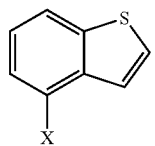

Formula XI wherein X is a leaving group
with piperazine compound of formula XII,

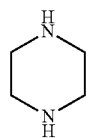

Formula XII to obtain a compound of formula XIII;

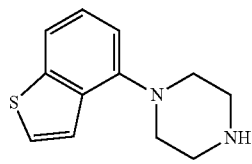

Formula XIII b. treating the compound of formula XIII with anhydrous hydrogen chloride to yield the compound of formula IV; and

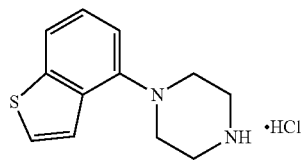

Formula IV c. isolating the compound of formula IV.

Figure 1:
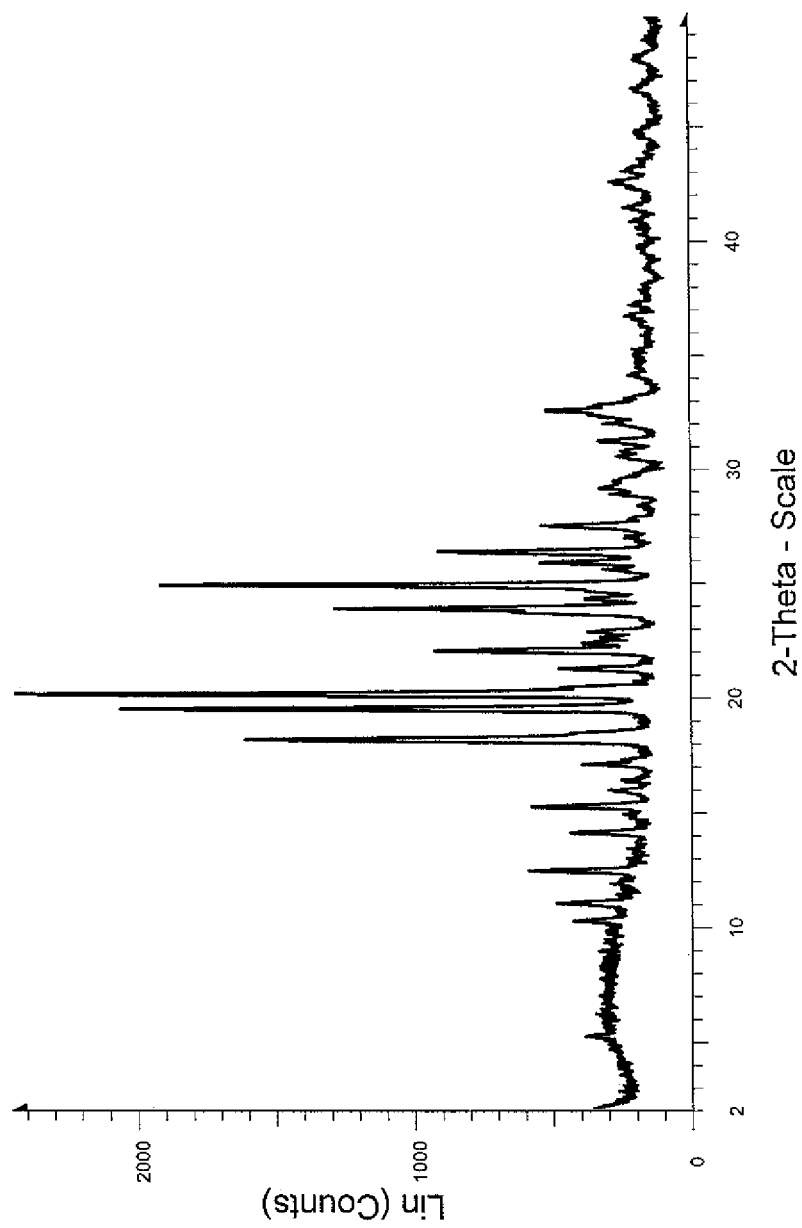
FIG. 1 shows powder X-ray diffractogram pattern of Brexpiprazole hydrochloride crystalline Form H.
Figure 2:
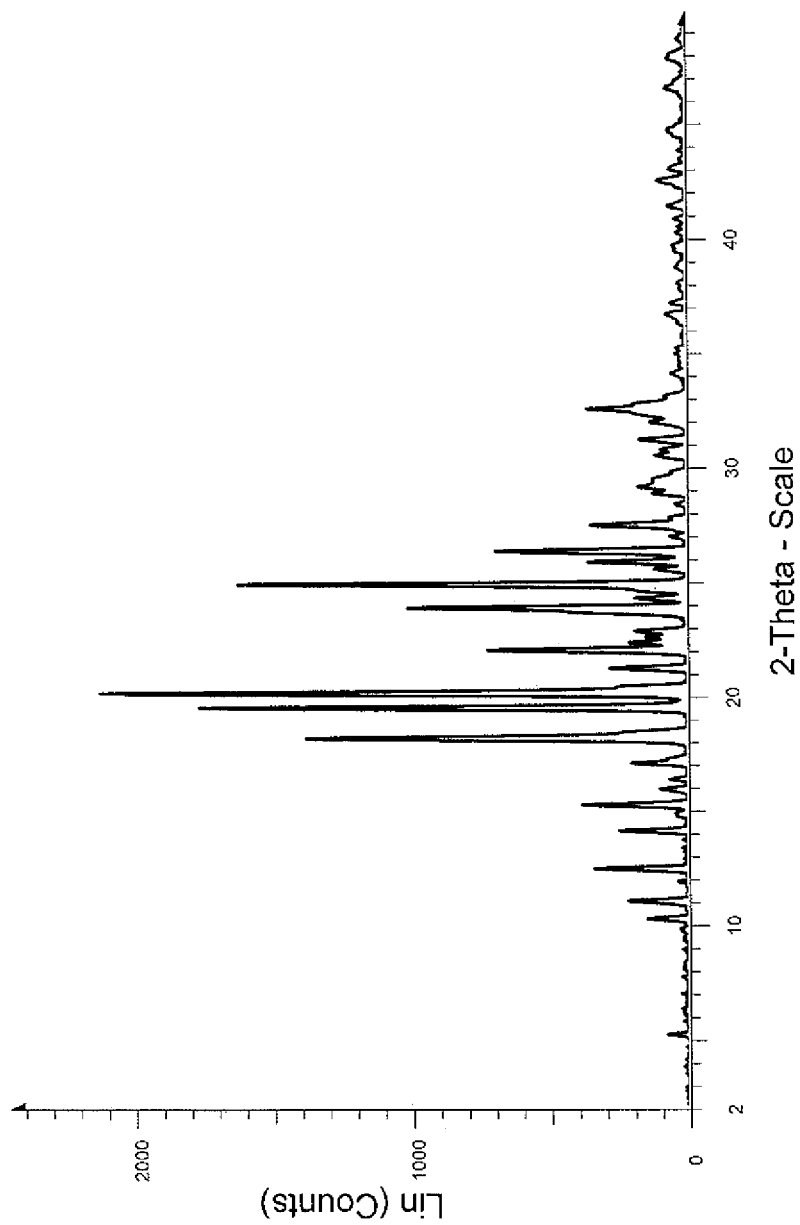
FIG. 2 shows powder X-ray diffractogram pattern of Brexpiprazole hydrochloride crystalline Form H.

X-ray powder diffraction spectrum was measured on a bruker axs D8 advance X-ray powder diffractometer having a copper-α radiation. Adequate sample was gently flattered on a sample holder and scanned from 2 to 50 degrees two-theta, at 0.02 increment and scan speed of 0.2 Sec/Step. The sample was simply placed on the sample holder. The sample was rotated at 30 rpm at a voltage 40 KV and current 35 mA.

DETAILED DESCRIPTION OF THE INVENTION

In an aspect of the present invention, Brexpiprazole hydrochloride crystalline Form H is characterized by Powder X-Ray Diffraction, having peaks at about 12.5, 15.3, 18.2, 20.2°2θ±0.2 degrees, further characterized by having the peaks at 19.5, 25.0°2θ±0.2 degrees.

In another aspect of the present invention provides a process for the preparation of Brexpiprazole hydrochloride crystalline Form H, which comprises treating Brexpiprazole base in a solvent, wherein the solvent is polar protic solvent; adjusting the pH to 1.0 to 2 with anhydrous hydrogen chloride, wherein hydrogen chloride gas is purged in an organic solvent; and isolating Brexpiprazole hydrochloride crystalline Form H.

In another aspect of the present invention provides to a process for the preparation of Brexpiprazole Hydrochloride, which comprises: reacting compound of formula V with 2,3-dichloro-5,6-dicyano-1,4-benzoquinone in the presence of an organic solvent selected from polar aprotic solvent, at a temperature of 30-60° C. and having molar ratio of 2,3-dichloro-5,6-dicyano-1,4-benzoquinone to compound of formula V in the range of 0.5-2:1 to obtain a compound of formula II; condensing the compound of formula II with compound of formula VI to yield a compound of formula III in the presence of a base; reacting the compound of formula XI with piperazine compound of formula XII to obtain a compound of formula XIII; treating the compound of formula XIII with anhydrous hydrogen chloride in an organic solvent to yield a compound of formula IV wherein the hydrogen chloride gas is purged in an organic solvent; optionally desalifying compound of formula IV; condensing the compound of formula IV or hydrochloride salt with formula III in the presence of a base and alkaline metal iodide to yield Brexpiprazole compound of formula I; converting obtained Brexpiprazole compound of formula I in to Brexpiprazole hydrochloride.

In another aspect of the present invention provides a process for the preparation of Brexpiprazole compound of formula I, which comprises treating Brexpiprazole hydrochloride Form H with a base, wherein base is selected from organic base or inorganic base.

In another aspect of the present invention provides to a process for the preparation of Brexpiprazole compound of Formula I, which comprises: reacting compound of formula V with 2,3-dichloro-5,6-dicyano-1,4-benzoquinone in the presence of an organic solvent selected from polar aprotic solvent, at a temperature of 30-60° C. and having molar ratio of 2,3-dichloro-5,6-dicyano-1,4-benzoquinone to compound of formula V is 0.5-2:1 to obtain a compound of formula II; condensing the compound of formula II with compound of formula VI to yield a compound of formula III in the presence of a base; condensing the compound of formula III with compound of formula IV or free base in the presence of a base and alkaline metal iodide to yield the compound of formula I and optionally converting the following:
  Brexpiprazole compound of formula I to Brexpiprazole hydrochloride
  isolating Brexpiprazole hydrochloride Form H
  converting to Brexpiprazole hydrochloride Form H to Brexpiprazole.

In another aspect of the present invention relates to a process for the preparation of 7-Hydroxyquinoline-2(1H)-one of formula II, which comprises reacting the compound of formula V with 2,3-dichloro-5,6-dicyano-1,4-benzoquinone in the presence of an organic solvent, wherein organic solvent is selected from polar aprotic solvent, at a temperature of 30-60° C. and having molar ratio of 2,3-dichloro-5,6-dicyano-1,4-benzoquinone to compound of formula V in the range of 0.5-2:1.

In another aspect of the present invention relates to a process for the preparation of Brexpiprazole, which comprises reacting the compound of formula XI with piperazine compound of formula XII to obtain a compound of formula XIII; treating the compound of formula XIII with anhydrous hydrogen chloride in an organic solvent to yield a compound of formula IV, wherein the hydrogen chloride gas is purged in an organic solvent; optionally desalifying compound of formula IV; condensing the compound of formula IV or free base with formula III in the presence of a base and alkaline metal iodide to yield compound of formula I and optionally converting the following:

Brexpiprazole compound of formula I to Brexpiprazole hydrochloride isolating Brexpiprazole hydrochloride Form H converting to Brexpiprazole hydrochloride Form H to Brexpiprazole.

In another aspect of the present invention relates to a process for the preparation of 1-(Benzo[b]thiophen-4-yl)piperazine Hydrochloride of formula IV, which comprises reacting the compound of formula XI with piperazine compound of formula XII to obtain a compound of formula XIII and treating the compound of formula XIII with anhydrous hydrogen chloride in an organic solvent to yield a compound of formula IV, wherein hydrogen chloride gas is purged in an organic solvent; and isolating the compound of formula IV.

In another aspect of the present invention, the reaction of compound of formula V with 2,3-Dichloro-5,6-dicyano-1,4-benzoquinone is maintained depending upon the reaction conditions.

In another aspect of the present invention, the molar ratio of 2,3-dichloro-5,6-dicyano-1,4-benzoquinone to compound of formula V is preferably 1:1.

In another aspect of the present invention, polar protic solvents are selected from group comprising of water, alcohols or mixtures thereof.

In another aspect of the present invention wherein hydrogen chloride gas is purged in an organic solvent selected from alcohol, ether or ester.

In another aspect of the present invention, the condensation of compound of formula II and formula VI is performed without solvent or in an inert solvent in the absence or presence of a base.

In another aspect of the present invention, the condensation of compound of formula III and formula IV is performed without solvent or in an inert solvent or polar aprotic solvent.

In another aspect of the present invention, the polar aprotic solvent used throughout the invention are selected from the group comprising of ketones, esters, nitriles, ethers, tetrahydrofuran, dimethyl sulfoxide, dimethyl formamide.

In another aspect of the present invention, ketones used throughout the invention are aliphatic ketones selected from the group comprising acetone, diethyl ketone, methyl ethyl ketone, methyl isobutyl ketone and methyl propyl ketone, cyclobutanone, cyclopentanone, cyclohexanone or mixtures thereof; esters used throughout the invention are aliphatic esters or aromatic esters wherein aliphatic esters are selected from ethyl acetate, methyl acetate, isopropyl acetate, tert-butyl methyl acetate, ethyl formate or mixtures thereof; nitriles used throughout the invention are selected from the group comprising of aliphatic nitriles such as $C_2$-$C_8$ nitrile; ethers used throughout the invention are selected from the group comprising of symmetrical or asymmetrical ethers or cyclic ethers selected from diethyl ether, methyl tert-butyl ether, diisopropyl ether or mixtures thereof; alcohols are selected from methanol, ethanol, n-propanol, isopropanol, n-butanol, pentanol, isobutanol or mixtures thereof.

In another aspect of the present invention, the base used throughout the invention is selected from inorganic base or organic base wherein inorganic bases are selected from the group comprising of ammonium hydroxide, alkali metal hydroxides such as sodium hydroxide, potassium hydroxide, cesium hydroxide, lithium hydroxide; alkali metal carbonates such as sodium carbonate, potassium carbonate, cesium carbonate, lithium carbonate; alkaline metal hydrogen carbonates such as lithium hydrogen carbonate, sodium hydrogen carbonate, potassium bicarbonate; sodium amide, sodium hydride, potassium hydride and alkaline metal alcoholates such as sodium methoxide, sodium ethoxide, potassium methoxide, potassium ethoxide; alkaline metals such as sodium, potassium; organic bases such as triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO).

In another aspect of the present invention halogens are selected from fluorine atom, chlorine atom, bromine atom and iodine atom.

In another aspect of the present invention examples of a group, which causes a substitution reaction the same as in a halogen atom include a lower alkanesulfonyloxy group, an arylsulfonyloxy group and an aralkylsulfonyloxy group.

In another aspect of the present invention alkanesulfonyloxy group is selected from methanesulfonyloxy, ethanesulfonyloxy, n-propanesulfonyloxy, isopropanesulfonyloxy, n-butanesulfonyloxy, tert-butanesulfonyloxy, n-pentanesulfonyloxy and n-hexanesulfonyloxy groups; arylsulfonyloxy group is selected from phenylsulfonyloxy, 4-methylphenylsulfonyloxy, 2-methylphenylsulfonyloxy, 4-nitrophenylsulphonyloxy, 4-methoxyphenylsulfonyloxy, 2-nitrophenylsulphonyloxy, 3-chlorophenylsulphonyloxy groups, naphthylsulfonyloxy group; aralkylsulfonyloxy group is selected from benzylsulfonyloxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy, α-naphthylmethyl sulfonyloxy, β-naphthylmethyl sulfonyloxy groups.

Examples of an inert solvent include water; ethers such as dioxane, tetrahydrofuran, diethyl ether, diethylene glycol dimethyl ether, ethylene glycol dimethyl ether; aromatic hydrocarbons such as benzene, toluene, xylene; lower alcohols such as methanol, ethanol, isopropanol; ketones such as acetone, methyl ethyl ketone; polar solvents such as N,N-dimethylformamide (DMF), dimethylsulfoxide (DMSO), hexamethylphosphoric triamide, acetonitrile.

In another aspect of the present invention the condensation of compound of formula III and formula IV is performed in the presence of alkaline metal iodide.

In another aspect of the present invention, alkaline metal iodide is selected from potassium iodide, sodium iodide.

In another aspect of the present invention, dimer impurity of formula X is less than 0.1% in 1-(benzo[b]thiophen-4-yl)piperazine Hydrochloride of formula IV.

In another aspect of the present invention the reaction of formula XI with formula XII is carried out in the presence of sodium tert-butoxide, (R)-(+)-2,2'-bis(diphenylphosphino)-1,1'-binaphthyl (BINAP) and tris(dibenzylideneacetone)dipalladium (0).

In another aspect of the present invention, the reaction of formula XI with formula XII is carried out in the presence of a solvent, selected from toluene.

In another aspect of the present invention, desalification is carried out by conventional methods.

In another aspect of the present invention, the reactions are maintained at the temperature depending on the reaction conditions.

In another aspect of the present invention, Brexpiprazole is prepared from Brexpiprazole hydrochloride crystalline form of the present invention or from the prior art polymorphs.

In another aspect of the present invention, Brexpiprazole or its salts are prepared by using the compound of formula IV of the present invention or obtained from the prior art.

In the present invention abbreviations used have the meanings as below:
DBN: 1,5-diazabicyclo[4.3.0]nonene-5
DBU: 1,8-diazabicyclo[5.4.0]undecene-7
DABCO: 1,4-diazabicyclo[2.2.2]octane
DDQ: 2,3-Dichloro-5,6-dicyano-1,4-benzoquinone In the following section embodiments are described by way of examples to illustrate the process of invention. However, these do not limit the scope of the present invention. Variants of these examples would be evident to persons ordinarily skilled in the art.

EXAMPLES

Reference Example—1

Preparation of Brexpiprazole
Preparation of 7-Hydroxyquinoline-2(1H)-one

N-(3-methoxyphenyl)cinnamamide (18 g, 71 mmol) was added AlCl$_3$ (28.4 g, 213 mmol) and the mixture heated at 180° C. for 5 min and then at 120° C. for 2 h. The mixture was then poured into ice and the resulting precipitate was collected by filtration, washed with water, and purified by flash chromatography eluting with dichloromethane:methanol (60:1) to give the title compound as a white solid.

Preparation of 7-(4-Chlorobutoxy)-1H-quinolin-2-one

After 14.7 g of potassium hydroxide was added to a methanol (250 ml) suspension of 30 g of 7-hydroxy-1H-quinolin-2-one, which was stirred at 50° C. to form a solution, 65 ml of 1-bromo-4-chlorobutane was added thereto and refluxed for 8 hours. After cooling to room temperature, precipitated crystals were separated by filtration. They were purified by silica gel column chromatography (dichloromethane:methanol=100:3), and 29.6 g of 7-(4-chlorobutoxy)-1H-quinolin-2-one was obtained in the form of a white powder.

Preparation of Brexpiprazole

A mixture of 9.0 g of 7-(4-chlorobutoxy)-1H-quinolin-2-one, 10 g of 1-benzo[b]thiophene-4-yl-piperazine hydrochloride, 14 g of potassium carbonate, 6 g of sodium iodide and 90 ml of dimethylformamide was stirred for 2 hours at 80° C. Water was added to the reaction solution and precipitated crystals were separated by filtration. The crystals were dissolved in a mixed solvent of dichloromethane and methanol, dried over magnesium sulfate, and the solvent was evaporated under reduced pressure. The residue was purified by silica gel column chromatography (dichloromethane:methanol=100:3). Recrystallized from ethanol, 13.6 g of Brexpiprazole in the form of a white powder was obtained.

Reference Example—2

Preparation of Brexpiprazole
Preparation of 1-benzo[b]thiophene-4-yl-piperazine hydrochloride A mixture of 14.4 g of 4-bromobenzo[b]thiophene, 29.8 g of piperazine anhydride, 9.3 g of sodium t-butoxide, 0.65 g of (R)-(+)-2,2'-bis(diphenylphosphino)-1,1'-binaphthyl (BINAP), 0.63 g of dipalladium tris(dibenzylideneacetone) and 250 ml of toluene was refluxed for 1 hour under nitrogen atmosphere. Water was poured to the reaction solution, which was then extracted with ethyl acetate and, after washed with water, dried over magnesium sulfate, and the solvent was evaporated under reduced pressure. The residue was purified by silica gel column chromatography (dichloromethane:methanol:25% ammonia water=100:10:1), and 9.5 g of 1-benzo[b]thiophen-4-yl-piperazine in the form of yellow oil was obtained.

3.7 ml of concentrated hydrochloric acid was added to a methanol solution of 9.5 g of 1-benzo[b]thiophen-4-yl-piperazine, and the solvent was evaporated under reduced pressure. Ethyl acetate was added to the residue and precipitated crystals were filtrated and recrystallized from methanol and 1-benzo[b]thiophen-4-yl-piperazine hydrochloride was obtained as colorless needle-like crystals.
Dimer Impurity: 0.2%

Preparation of Brexpiprazole

A mixture of 9.0 g of 7-(4-chlorobutoxy)-1H-quinolin-2-one, 10 g of 1-benzo[b]thiophene-4-yl-piperazine hydrochloride, 14 g of potassium carbonate, 6 g of sodium iodide and 90 ml of dimethylformamide was stirred for 2 hours at 80° C. Water was added to the reaction solution and precipitated crystals were separated by filtration. The crystals were dissolved in a mixed solvent of dichloromethane and methanol, dried over magnesium sulfate, and the solvent was evaporated under reduced pressure. The residue was purified by silica gel column chromatography (dichloromethane:methanol=100:3). Recrystallized from ethanol, 13.6 g of Brexpiprazole in the form of a white powder was obtained.

Example 1

Preparation of 7-Hydroxyquinolin-2(1H)-one

Charged 7-Hydroxy-3,4-dihydroquinolin-2(1H)-one (100 g), tetrahydrofuran (1000 ml) and stirred for 15 minutes at 25-30° C. Added 2,3-dichloro-5,6-dicyano-1,4-benzoquinone (180 gm) lot wise for 60 minutes, heated to 35-40° C. and stirred for 5 hours to 6 hours. Cooled to 25-30° C., filtered the solid and washed with tetrahydrofuran. The wet solid was taken in methanol, stirred for 45 minutes at 60-65° C. and cooled to 25-30° C. Filtered the solid thus obtained and dried to yield 90 gm of 7-Hydroxyquinolin-2(1H)-one.

Example 2

Preparation of 7-(4-Bromobutoxy)quinoline-2(1H)-one

Charged 7-Hydroxyquinolin-2(1H)-one (90 g), methanol and stirred for 15 minutes at 25-30° C. Added potassium hydroxide (38 g) lot wise for 15 minutes and stirred at 25-30° C. Further added 1,4-dibromobutane (360 g), heated to reflux and stirred for 14 hours to 15 hours at reflux. Cooled to 15-20° C., stirred and filtered. Filtrate was distilled off, methanol was added at 55-60 deg C. and stirred. Further cooled to 25-30° C. and filtered. The solid thus obtained was taken in methanol, water and heated to 60-65° C. and stirred for 30 minutes. Stirred for 2 hours at 0-5° C. and filtered the solid and dried to yield 72 g of 7-(4-Bromobutoxy)quinoline-2(1H)-one.

Example 3

Preparation of 1-benzo[b]thiophene-4-yl-piperazine hydrochloride

A mixture of 100 g of 4-bromobenzo[b]thiophene, 206 g of piperazine anhydride, 64.5 g of sodium t-butoxide, 4 g of (R)-(+)-2,2'-bis(diphenylphosphino)-1,1'-binaphthyl (BINAP), 4 g of dipalladium tris(dibenzylideneacetone) and 1000 ml of toluene were refluxed for 1 hour. Cooled to 25-30° C., water and ethyl acetate were added to the reaction mass, stirred and separated the layers. Organic layer was dried, distilled and co-distilled with methanol. Added methanol and filtered the mass on hiflo bed. The pH of the filtrate was adjusted to 1.5 to 2.0 with 6% methanol. HCl, stirred and the separated solid was filtered and dried to yield 90 g of 1-benzo[b]thiophene-4-yl-piperazine hydrochloride.

Dimer impurity: 0.08%

Example 4

Preparation of Brexpiprazole

Charged 75 g of sodium iodide to a mixture of 94.5 g of 7-(4-Bromobutoxy)-1H-quinolin-2-one in 1170 ml of acetonitrile. Heated to 80° C. and stirred. Cooled to 25-30° C. and added 90 g of 1-benzo[b]thiophene-4-yl-piperazine hydrochloride and 120.6 ml of triethylamine. Stirred for 5 hours at 80° C. and cooled to 25-30° C. Stirred, filtered the solid and dried to yield 140 g of the title compound (Purity by HPLC: 99.4%).

Example 5

Preparation of Brexpiprazole Hydrochloride Form H

Charged Brexpiprazole (140 g) in 1400 ml of Methanol and stirred. The pH of the reaction mass was adjusted to 1.5 to 2.0 with 350 ml of 6% methanolic. HCl and stirred for 1 hour. The solid thus separated was filtered and washed with methanol and dried to yield Form H of Brexpiprazole hydrochloride (90 gm).

Example 6

Preparation of Brexpiprazole from Brexpiprazole hydrochloride

Brexpiprazole hydrochloride (110 gm) was taken in methylene dichloride and water and stirred for 15 minutes. The pH of the reaction mass was adjusted to 8.0 to 8.5 with ammonia solution and stirred. Separated the layers and organic layer was dried, distilled and co-distilled with ethanol. Ethanol was added to the residue, heated to 70° C. and stirred, further cooled to 25-30° C. Stirred, filtered the solid, washed and dried to yield 80 g of title compound (Purity by HPLC: 99.8%).

Example 7

Preparation of Brexpiprazole

Charged Brexpiprazole (160 g) in methanol and stirred. The pH of the reaction mass was adjusted to 1.0 to 1.5 with 400 ml of methanolic. HCl, heated to 60-65° C. and stirred for 30 minutes. The solid thus separated was filtered and washed with methanol. The wet solid was taken in methylene dichloride and water and stirred for 15 minutes. The pH of the reaction mass was adjusted to 8.5 to 9.0 with ammonia solution and stirred. Separated the layers and organic layer was treated with carbon, filtered through hiflo and filtrate was added ethanol. Distilled off the solvent until the temperature reached 75-80° C. and stirred, further cooled to 25-30° C., stirred for 2 hours at 25-30° C., filtered the solid, washed and dried to yield 100 g of title compound.

We claim:

1. Brexpiprazole hydrochloride Form H characterized by Powder X-Ray Diffraction, having the characteristic peaks at 12.5, 15.3, 18.2, 20.2°±0.2°2θ.

2. A process for the preparation of Brexpiprazole hydrochloride Form H of claim 1, which comprises:
   a. stirring Brexpiprazole base in methanol;
   b. adjusting the pH to 1.5 to 2.0 with methanolic anhydrous hydrogen chloride; and
   c. isolating Brexpiprazole hydrochloride crystalline Form H by filtration.

3. The process for the preparation of Brexpiprazole Hydrochloride, which comprises:
   a. reacting compound of formula V,

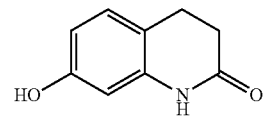

Formula V with 2,3-dichloro-5,6-dicyano-1,4-benzoquinone to obtain a compound of formula II;

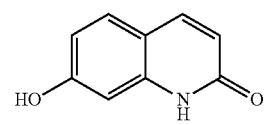

Formula II b. condensing the compound of formula II with compound of formula VI,

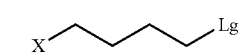

Formula VI wherein X, Lg represents a halogen atom or a group which causes a substitution reaction the same as in halogen atom to yield a compound of formula III;

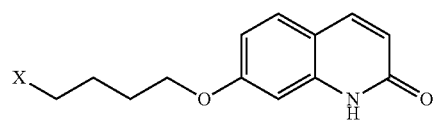

Formula III c. reacting the compound of formula XI,

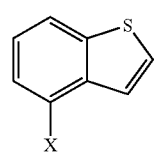

Formula XI wherein X is a leaving group with piperazine compound of formula XII,

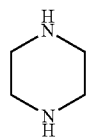
Formula XII to obtain a compound of formula XIII;

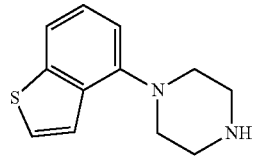
Formula XIII d. treating the compound of formula XIII with anhydrous hydrogen chloride to yield a compound of formula IV;

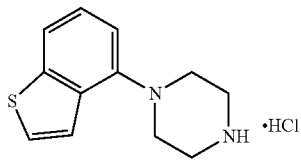
Formula IV e. optionally desalifying compound of formula IV;
f. condensing the compound of formula IV obtained as in step (d) or step (e) with formula III,

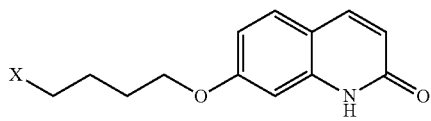
Formula III wherein X is a leaving group
to yield Brexpiprazole compound of formula I; and
g. preparing Brexpiprazole hydrochloride Form H of with the process of claim 2.

4. A process for the preparation of 7-Hydroxyquinoline-2(1H)-one of formula II, which comprises:

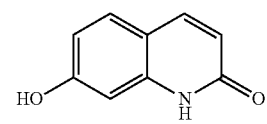
Formula II reacting the compound of formula V,

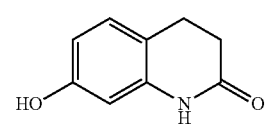
Formula V with 2,3-dichloro-5,6-dicyano-1,4-benzoquinone in tetrahydrofuran.

5. The process according to claim 3, a process for the preparation of Brexpiprazole compound of Formula I, which comprises:

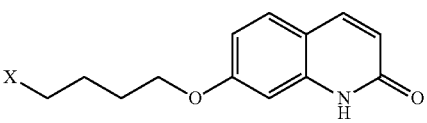
Formula I a. reacting compound of formula V

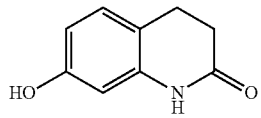
Formula V with 2,3-dichloro-5,6-dicyano-1,4-benzoquinone in the presence of an organic solvent selected from polar aprotic solvent, at a temperature of 30-60° C. and having molar ratio of 2,3-dichloro-5,6-dicyano-1,4-benzoquinone to compound of formula V in the range of 0.5-2:1 to obtain a compound of formula II;

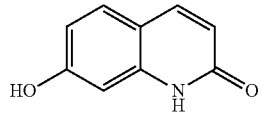
Formula II b. condensing the compound of formula II with compound of formula VI,

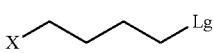
Formula VI wherein X, Lg represents a halogen atom or a group which causes a substitution reaction the same as in halogen atom to yield a compound of formula III;

Formula III

X⌒⌒⌒O-[quinolinone]

c. condensing the compound of formula III with compound of formula IV or free base;

Formula IV to yield the compound of formula I;
d. converting Brexpiprazole compound of formula I to Brexpiprazole hydrochloride;
e. isolating Brexpiprazole hydrochloride Form H characterized by Powder X-Ray Diffraction, having the characteristic peaks at 12.5, 15.3, 18.2, 20.2°±0.2°2θ; and
f. converting Brexpiprazole hydrochloride to Brexpiprazole;
wherein steps d to f are optional, wherein the condensation of compound of formula II with formula VI and formula III with formula IV or its free base is carried out in the presence or absence of a base.

6. The process according to claim 5, process for the preparation of Brexpiprazole compound of Formula I, Formula I which comprises, preparing Brexpiprazole hydrochloride Form H of with the process of claim 2.

7. The process according to claim 6, wherein the base is selected from inorganic base selected from the group comprising of ammonium hydroxide, alkali metal hydroxides selected from sodium hydroxide, potassium hydroxide, cesium hydroxide, lithium hydroxide; alkali metal carbonates selected from sodium carbonate, potassium carbonate, cesium carbonate, lithium carbonate; alkaline metal hydrogen carbonates selected from lithium hydrogen carbonate, sodium hydrogen carbonate, potassium bicarbonate; sodium amide, sodium hydride, potassium hydride and alkaline metal alcoholates, selected from sodium methoxide, sodium ethoxide, potassium methoxide, potassium ethoxide; alkaline metals selected from sodium, potassium; organic bases selected from triethylamine, tripropylamine, pyridine, quinoline, piperidine, imidazole, N-ethyldiisopropylamine, dimethylaminopyridine, trimethylamine, dimethylaniline, N-methylmorpholine, 1,5-diazabicyclo [4.3.0]nonene-5 (DBN), 1,8-diazabicyclo [5.4.0]undecene-7(DBU), 1,4-diazabicyclo [2.2.2]octane (DABCO).

8. The process according to claim 5, a process for the preparation of Brexpiprazole compound of Formula I, Formula I which comprises:
a. reacting the compound of formula XI, Formula XI wherein X is a leaving group
with piperazine compound of formula XII, Formula XII to obtain a compound of formula XIII;

Formula XIII b. treating the compound of formula XIII with anhydrous hydrogen chloride to yield a compound of formula IV;

Formula IV c. optionally desalifying compound of formula IV;
d. condensing the compound of formula IV obtained as in step (b) or step (c) with formula III, Formula III wherein X is a leaving group
to yield a compound of formula I;
e.
f. preparing Brexpiprazole hydrochloride Form H of with the process of claim 2;
g. converting Brexpiprazole hydrochloride Form H to Brexpiprazole;
wherein steps e to g are optional.

9. The process according to claim 8, a process for the preparation of 1-(benzo[b]thiophen-4-yl)piperazine hydrochloride salt of formula IV, which comprises:

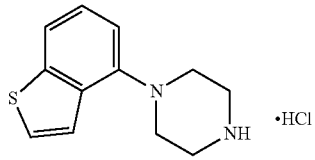

Formula IV a. reacting the compound of formula XI,

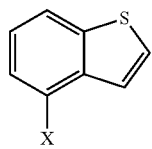

Formula XI wherein X is a leaving group
with piperazine compound of formula XII,

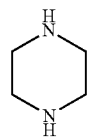

Formula XII to obtain a compound of formula XIII; and

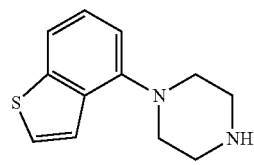

Formula XIII b. treating the compound of formula XIII with anhydrous hydrogen chloride to yield the compound of formula IV; and

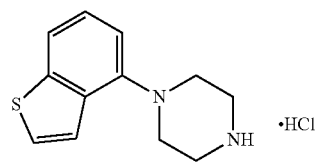

Formula IV c. isolating the compound of formula IV.

* * * * *